United States Patent [19]

Darby

[11] Plant 5,209

[45] Mar. 20, 1984

[54] HIBISCUS PLANT NAMED "ANNE ARUNDEL"

[76] Inventor: Robert H. Darby, Oaknoll, Apt. S-432, 701 Oaknoll Dr., Iowa City, Iowa 52240

[21] Appl. No.: 422,878

[22] Filed: Sep. 24, 1982

[51] Int. Cl.[3] ..... A01H 5/00

[52] U.S. Cl. ..... Plt./68

[58] Field of Search ..... Plt./68

*Primary Examiner*—Robert E. Bagwill

[57] ABSTRACT

The present invention is a new and distinct Hibiscus plant cultivar named "Anne Arundel," resulting from a definite effort, over a period of time, to produce by hybridization and selection a clear pink of elegant form and substance, a plant of great landscape value blooming profusely from midsummer to frost, a plant as excellent in its way as the brilliant red Hibiscus "Lord Baltimore" and the pink-and-red bicolor Hibiscus "Lady Baltimore" (U.S. Plant Pat. No. 4,271).

2 Drawing Figures

BACKGROUND OF THE NEW PLANT

The objective of this breeding program was primarily to develop a plant with the following characteristics:

(a) Decorative and unobtrusive foliage, sparse enough to permit close underplanting with annuals or perennials.

(b) A clear pink flower of real elegance rather than mere size.

(c) A plant of medium size, of good form and habit, and of good landscaping quality.

The hybridization was conducted over a period of years using as seed parent "Lady Baltimore," which first bloomed in 1972. The ancestry of "Lady Baltimore" includes *Hibiscus militaris, Hibiscus coccineus, Hibiscus moscheutos,* and *Hibiscus palustris.* As far as possible, pollen was exclusively delivered from selected pink-flowered hibiscus plants of many varieties, all of which had one or more poor qualities (coarse, hairy foliage; stiff, heavy flowers; sprawling habit of growth; and so forth). Selections were continuously made from the seedlings so derived, and the best of these were used for backcrossing.

The new plant produced its first flower in the summer of 1977, and because of the beautiful coloring and substance of its blooms, together with its attractive foliage and habit of growth, it was selected for reproduction and test. Asexual propagation of this new plant by cuttings and division was carried on at College Park, Md., and observation of the progeny of the original plant has demonstrated that this new variety has fulfilled the objective and that its distinctive characteristics are firmly fixed and hold true from generation to generation vegetatively propagated from the original clone.

DESCRIPTION OF THE DRAWINGS

This new variety of hibiscus plant is illustrated by the accompanying full color photographic drawings which show, first, the fully opened flower, the colors being as true as can be reasonably done by conventional photographic procedures; and second, some typical leaves.

DESCRIPTION OF THE NEW PLANT

The following is a detailed description of the new variety, color terminology being in accordance with *The Royal Horticultural Society Colour Chart* (indicated by initials R.H.S. plus number) or with ordinary dictionary significance.

THE PLANT

Type: Tender; herbaceous perennial.
Classification: Hybrid variety of hibiscus.
Origin: Seedling.
Parentage:
- *Seed parent.*—Hibiscus "Lady Baltimore" (U.S. Plant Pat. No. 4,271).
- *Pollen parent.*—Unknown (from selected progeny of "Lady Baltimore" crossed with various pink-flowered varieties of hibiscus).

Propagation: Holds its distinguishing characteristics through succeeding propagations by cuttings and division.
Form: Bushy annual growth from perennial roots.
Habit: Upright and much branched.
Growth: Vigorous and moderately free.
Leaves: Moderately abundant; finely cut; decorative.
- *Margins.*—Length two to seven inches; irregularly serrate.
- *Color.*—Medium green. Underside of leaves — light green. New leaves — light green and shiny.
- *Petiole.*—Length one to seven inches. Lenticels — none.
- *Form.*—Mostly three- to five-parted; palmately lobed.
- *Stipules.*—None.

Stem: Light green when young, aging to red.
Height: Medium — four to five feet.

THE FLOWER

Date described: Aug. 27, 1982

Blooming habit: Continuous and free blooming.
Petals:
- *Length.*—Four-and-a-half to five inches.

Diameter: Nine to ten inches.
Shape: Widely flared bell, with petals overlapping and ruffled.
Stamen tube:
- *Color.*—White.

Filaments:
- *Color.*—On lower part of tube, crimson (R.H.S. 52A); on upper part of tube, white.

Stamens: Numerous.
Stigma:

*Color.*—Whitish, with fine setae providing overtones of light neyron rose (app. R.H.S. 55D).

Style:

*Color.*—White.

Base of pistil or very center of throat:

*Color.*—White, with base of each petal "intruding" a crimson column about one-third inch up the enlarged area surrounding the ovary.

Pollen:

*Color.*—Greyed magenta rose (app. R.H.S. 186C).

Petalage:

*Single.*—Five petals arranged regularly, overlapping and ruffled.

Shape of petals: Broadly obovate (almost reniform), recurved at base to form slight green star of revealed calyx.

Aspect of flower: Central one-third — satiny; outer two-thirds — velvety.

Texture: Leathery and moderately thick.

Color of flower:

*Inside.*—Large satiny crimson center (R.H.S. 52A) comprising about one-fifth of each petal, then a band of light neyron rose (R.H.S. 55D) approximately one-half inch wide, shading into an outer velvety dark neyron rose area (R.H.S. 62A). General effect is of a tricolor: red eye surrounded by pale pink zone, shading into glowing hot-pink outer area. Petals are heavily veined and reticulated, but color in each of the three areas is relatively solid. Underlying all three colors is a suggestion of bluish lavender that simply does not appear in the R.H.S. chart.

*Outside.*—Light- and dark-pink pinwheel effect (app. R.H.S. 62D shading into R.H.S. 62A), with base of each petal almost white with greenish overcast.

Calyx: Five-toothed, light yellowish green.

Bractlets: Medium green.

Flowers: Numerous; elegant in appearance; individual flower lasting one day.

Blooming period: July to frost. When all buds on an individual branch have bloomed, new growth with new buds develops. From the onset of the blooming period, the plant is seldom without flowers.

Peduncle:

*Length.*—Three to five inches; medium thickness; stiff.

Stipules: None.

I claim:

1. A new and distinctive cultivar of hibiscus substantially as herein shown and described, having a pink flower of elegant form and substance, a plant of great landscape value, blooming profusely from midsummer to frost.

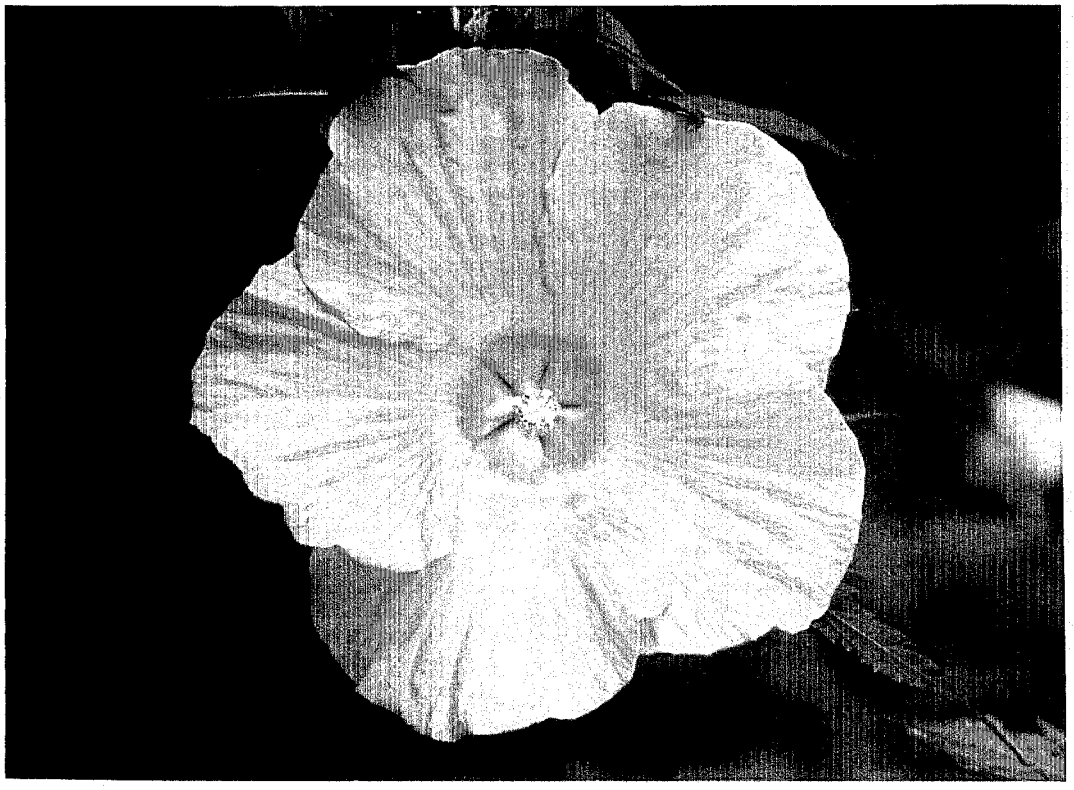
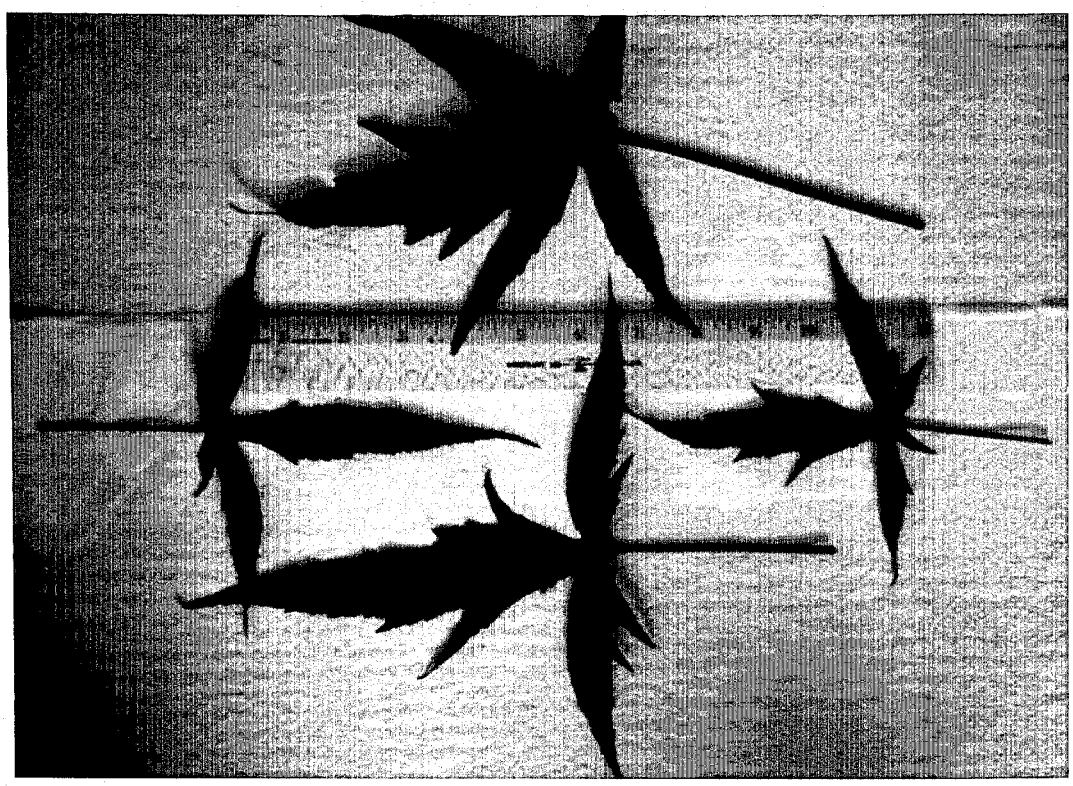

* * * * *